United States Patent [19]
Kaeding

[11] 4,016,219
[45] Apr. 5, 1977

[54] DISPROPORTIONATION OF TOLUENE

[75] Inventor: Warren W. Kaeding, Westfield, N.J.

[73] Assignee: Mobil Oil Corporation, New York, N.Y.

[22] Filed: Aug. 22, 1975

[21] Appl. No.: 606,810

[52] U.S. Cl. ............................................ 260/672 T
[51] Int. Cl.² .......................................... C07C 3/62
[58] Field of Search ............ 260/672 T; 208/DIG. 2

[56] References Cited
UNITED STATES PATENTS

| | | | |
|---|---|---|---|
| 3,417,157 | 12/1968 | Pollitzer .............................. | 260/672 |
| 3,551,510 | 12/1970 | Pollitzer et al. .................... | 260/672 |
| 3,651,162 | 3/1972 | Pohlmann et al. ................. | 260/672 |
| 3,790,471 | 2/1974 | Argauer et al. .................... | 260/672 |
| 3,808,284 | 4/1974 | Wallace et al. ..................... | 260/672 |

*Primary Examiner*—Delbert E. Gantz
*Assistant Examiner*—C. E. Spresser
*Attorney, Agent, or Firm*—Charles A. Huggett; Raymond W. Barclay

[57] ABSTRACT

Disproportionation of toluene to produce benzene and xylenes rich in the para isomer is accomplished by subjecting toluene to disproportionation conditions in the presence of a catalyst comprising a crystalline aluminosilicate zeolite, said zeolite having a silica to alumina ratio of at least about 12 and a constraint index, as hereinafter defined, within the approximate range of 1 to 12, said catalyst having been modified by the addition thereto of phosphorus in an amount of at least about 0.5 percent by weight.

13 Claims, No Drawings

DISPROPORTIONATION OF TOLUENE

BACKGROUND OF THE INVENTION

1. Field of the Invention

This invention relates to a process for disproportionation of toluene utilizing a phosphorus-containing crystalline aluminosilicate zeolite catalyst to yield benzene and xylenes in which the proportion of para-xylene isomer is substantially in excess of its normal equilibrium concentration.

2. Description of the Prior Art

The disproportionation of aromatic hydrocarbons in the presence of ziolite catalysts has been described by Grandio et al. in the Oil and Gas Journal, Vol. 69, Number 48 (1971).

U.S. Pat. Nos. 3,126,422; 3,413,374; 3,598,878; 3,598,879 and 3,607,961 show vapor-phase disproportionation ot toluene over various catalysts.

In these prior art processes, the xylene product produced has the equilibrium composition of approximately 24 percent of para, 54 percent of meta and 22 percent of ortho. Of the xylene isomers, i.e. ortho-, meta- and para-xylene, meta-xylene is the least desired product, with ortho- and para-xylene being the more desired products. Para-xylene is of particular value being useful in the manufacture of terephthalic acid which is an intermediate in the manufacture of synthetic fibers such as "Dacron". Mixtures of xylene isomers either alone or in further admixture with ethylbenzene have previously been separated by expensive superfractionation and multistage refrigeration steps. Such process, as will be realized, has involved high operation costs and has a limited yield.

SUMMARY OF THE INVENTION

In accordance with the present invention, there has been discovered a process for disproportionating toluene to yield benzene and xylenes rich in the para isomer, preferably wherein the para-xylene content is in excess of 50 weight percent of the reaction product, by subjecting toluene to disproportionation conditions in the presence of a catalyst comprising a crystalline aluminosilicate zeolite, such zeolite having a silica to alumina ratio of at least about 12, a constraint index within the approximate range of 1 to 12 and which has been modified to by the addition thereto of phosphorus in an amount of at least about 0.5 percent by weight.

The present process comprises disproportionation of toluene in the presence of the specified catalyst at a temperature between about 800° F. and about 1400° F. at a pressure between atmospheric and about 1000 psig utilizing a feed weight hourly space velocity (WHSV) between about 0.5 and about 20. The latter WHSV is based upon the weight of catalyst composition, i.e. total weight of active catalyst and binder therefor. The effluent is separated and distilled to remove the desired products of benzene and xylenes and unreacted product, i.e. toluene, is recycled for further reaction.

DESCRIPTION OF SPECIFIC EMBODIMENTS

The zeolite catalysts herein described are members of a novel class of zeolites exhibiting some unusual properties. These catalysts induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalyst, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3- methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 50%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} \text{ (fraction of n-hexane remaining)}}{\log_{10} \text{ (fraction of 3-methylpentane remaining)}}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts are:

| CAS | C.I. |
| --- | --- |
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. application Ser. No. 528,060, filed Nov. 29, 1974. This zeolite can be identified, in terms of mole ratios of oxides and in the anhydrous state, as follows:

$$(0.3-2.5)R_2O : (0-0.8)M_2O : Al_2O_3 : > 8\ SiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4-2.5)R_2O : (0-0.6)\ M_2O : Al_2O_3 : xSiO_2$$

wherein R is an organic nitrogen-containing cation derived from a 2-(hydroxyalkyl) trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d(A) | I/Io |
| --- | --- |
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

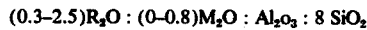

| R+ | Broad | Preferred |
|---|---|---|
| R+ + M+ | 0.2–1.0 | 0.3–0.9 |
| OH$^-$/SiO$_2$ | 0.05–0.5 | 0.7–0.49 |
| H$_2$O/OH$^-$ | 41–500 | 100–250 |
| SiO$_2$/Al$_2$O$_3$ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH$^-$ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. application Ser. No. 528,061, filed Nov. 29, 1974. This zeolite can be identified, in terms of mole ratios of oxides and in the anhydrous state, as follows:

(0.3–2.5)R$_2$O : (0–0.8)M$_2$O : Al$_2$O$_3$ : 8 SiO$_2$ wherein R is an organic nitrogen-containing cation derived from ethylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

(0.4–2.5)R$_2$O : (0.0.6) M$_2$O : Al$_2$O$_3$ : xSiO$_2$ wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d(A) | I/Io |
|---|---|
| 9.6 ± 0.20 | Very Strong - Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane(with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

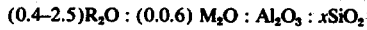

| R+ | Broad | Preferred |
|---|---|---|
| R+ + M+ | 0.2–1.0 | 0.3–0.9 |
| OH$^-$/SiO$_2$ | 0.05–0.5 | 0.7–0.49 |
| H$_2$O/OH$^-$ | 41–500 | 100–250 |
| SiO$_2$/Al$_2$O$_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH$^-$ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for 1 hour, for example, followed by base exchange with ammonium salts followed by calcination at 1000° F. in air. The presence or organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the Periodic Table. However, in the case of Group IA metals, the cation content should in no case be so large as to effectively inactivate the catalyst.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table including, by way of example, nickel, zinc, calcium or rare earth metals.

The crystals of zeolite in a form substantially free of alkali metal, i.e. containing less than about 1.5 weight percent alkali metal and preferably having at least a portion of the original cations associated therewith replaced by hydrogen, are then contacted with a phosphorus compound.

Representative phosphorus-containing compounds include derivatives of groups represented by $PX_3$, $RPX_2$, $R_2PX$, $R_3P$, $X_3PO$, $(XO_3)PO$, $(XO)_3P$, $R_3P=O$, $R_3P=S$, $RPO_2$, $PPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites, $(RO)PR_2$, and dialkyl alkylphosphonite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpyrophosphite. The alkyl groups in the mentioned compounds contain one to four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PX$, dialkylphosphionochloridites, $R_2PCl$, alkyl alkylphosphonochloridates, $(RO)(R)P(O)Cl$, dialkyl phosphinochoridates, $R_2P(O)Cl$ and $RP(O)Cl_2$. Applicable corresponding sulfur derivatives include $(RS)PCl_2$, $(RS)_2PX$, $(RS)(R)P(S)Cl$ and $R_2P(S)Cl$.

Preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchloro thiophosphate, methyl acid phosphate and other alcohol-$P_2O_5$ reaction products.

Reaction of the zeolite with the phosphorus compound is effected by contacting the zeolite with such compound. Where the treating phosphorus compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as n-octane may be employed. The phosphorus-containing compound may be used without a solvent, i.e., may be used as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite such as air or nitrogen or with an oganic solvent, such as octane or toluene.

Prior to reacting the zeolite with the phosphorus-containing compound, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation and prior to use is also preferred. The heating can be carried out in the presence of oxygen, for example air. Heating can be at a temperature of about 150° C. However, higher temperatures, i.e., up to about 500° C. are preferred. Heating is generally carried out for 3–5 hours but may be extended to 24 hours or longer. While heating temperatures above about 500° C. can be employed, they are not necessary. At temperatures of about 1000° C., the crystal structure of the zeolite tends to deteriorate.

The amount of phosphorus incorporated with the zeolite should be at least about 0.5 percent by weight. However, it is preferred that the amount of phosphorus in the zeolite be at least about 2 percent by weight when the same is combined with a binder, e.g. 35 weight percent of alumina. The amount of phosphorus can be as high as about 25 percent by weight or more depending on the amount and type of binder present. Preferably, the amount of phosphorus added to the zeolite is between about 0.7 and about 15 percent by weight.

The amount of phosphorus incorporated with the zeolite by reaction with elemental phosphorus or phosphorus-containing compound will depend upon several factors. One of these is the reaction time, i.e., the time that the zeolite and the phosphorus-containing source are maintained in contact with each other. With greater reaction times, all other factors being equal, a greater amount of phosphorus is incorporated with the zeolite. Other factors upon which the amount of phosphorus incorporated with the zeolite is dependent include reaction temperature, concentration of the treating compound in the reaction mixture, the degree to which the zeolite has been dried prior to reaction with the phosphorus-containing compound, the conditions of drying of the zeolite after reaction of the zeolite with the treating compound, and the amount and type of binder incorporated with the zeolite.

In practicing the desired disproportionation process it may be desirable to incorporate the modified zeolite in another material resistant to the temperatures and other conditions employed in the disproportionation process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occuring clays which can be composited with the modified zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided modified zeolite and inorganic oxide gel matrix may vary widely with the zeolite content ranging from between about 1 to about 99 percent by weight and more usually in the range of about 5 to about 80 percent by weight of the composite.

The process of this invention is conducted such that disproportionation of toluene is carried out in the vapor phase by contact in a reaction zone, such as, for example, a fixed bed of catalyst, under disproportionation effective conditions, said catalyst being characterized as above-described and preferably hydrogen exchanged such that a predominate portion of its exchangeable cations are hydrogen ions. In general, it is contemplated that more than 50 percent and preferably more than 75 percent of the cationic sites of the crystalline alumino-silicate zeolite, above-described, will be occupied by hydrogen ions.

The disproportionation process described herein may be carried out as a batch-type, semi-continuous or continuous operation utilizing a fixed or moving bed catalyst system. A preferred embodiment entails use of a fluidized catalyst zone wherein toluene is passed concurrently or countercurrently through a moving fluidized bed of the catalyst. The fluidized catalyst after use is conducted to a regeneration zone wherein coke is burned from the catalyst in an oxygen-containing atmosphere, e.g. air, at an elevated temperature, after which the regenerated catalyst is recycled to the conversion zone for further contact with the toluene feed.

Reactivation of the phosphorus modified zeolite catalyst can be effected by passing a vaporized phosphorus compound through the catalyst bed after the catalyst has been used for the desired disproportionation. Thus, for example, after a period of continued use of the catalyst, it can be revivified by passage therethrough of vaporized diphenyl phosphine chloride at an elevated temperature, i.e. about 250° C. over a ½ hour period of time. This treatment is then suitably followed by heating in air at 150 cc/minute/gram of catalyst at about 550° C. for approximately ½ hour.

The following examples will serve to illustrate the process of the invention without limiting the same:

EXAMPLE 1

This example serves to illustrate disproportionation of toluene in the presence of a catalyst of HZSM-5 which has not been modified with phosphorus.

A catalyst containing 65 weight percent acid ZSM-5 and 35 weight percent alumina was prepared as follows:

A sodium silicate solution was prepared by mixing 8440 lb. of sodium silicate (Q Brand — 28.9 weight percent $Na_2O$ and 62.2 weight percent $H_2O$) and 586 gallons of water. After addition of 24 lb. of a dispersant of a sodium salt of polymerized substituted benzenoid alkyl sulfonic acid combined with an inert inorganic suspending agent (Daxad 27), the solution was cooled to approximately 55° F. An acid alum solution was prepared by dissolving 305 lb. aluminum sulfate (17.2 $Al_2O_3$), 733 lb. sulfuric acid (93%) and 377 lb. sodium chloride in 602 gallons of water. The solutions were gelled in a mixing nozzle and discharged into a stirred autoclave. During this mixing operation, 1200 lb. of sodium chloride was added to the gel and thoroughly mixed in the vessel. The resulting gel was thoroughly agitated and heated to 200° F. in the closed vessel. After reducing agitation, an organic solution prepared by mixing 568 lb. tri-n-propylamine, 488 lb. n-propyl-bromide and 940 lb. methyl ethyl ketone was added to the gel. This mixture was reacted for 14 hours at a temperature of 200–210° F. At the end of this period, agitation was increased and these conditions maintained until the crystallinity of the product reached at least 65% ZSM-5 as determined by X-ray diffraction. Temperature was then increased to 320° F. until crystallization was complete. The residual organics were flashed from the autoclave and the product slurry was cooled.

The product was washed by decantation using a flocculant of polyammonium bisulfate. The washed product containing less than 1% sodium was filtered and dried. The weight of dried zoelite was approximately 2300 lb.

The dried product was mixed with alpha alumina monohydrate and water (65% zeolite, 35% alumina binder on ignited basis) then extruded to form of 1/16 inch pellet with particle density < 0.98 gram/cc and crush strength of > 20 lb./linear inch.

After drying, the extruded pellets were calcined in nitrogen (700–1000 SCFM) for 3 hours at 1000° F., cooled and ambient air was passed through the bed for 5 hours. The pellets were then ammonium exchanged for 1 hour at ambient temperature (240 lb. ammonium nitrate dissolved in approximately 800 gallons of deionized water). The exchange was repeated and the pellets washed and dried. Sodium level in the exchanged pellets was less than 0.05 weight percent.

The dried pellets were calcined in a nitrogen-air mixture (10–12.5% air — 90–87.5% nitrogen) for 6 hours at 1000° F. and cooled in nitrogen alone.

This catalyst was used for disproportionating toluene by passing the same over 6.0 grams of the catalyst at a weight hourly space velocity of 3.5–3.6 at a temperature between 450° C. and 600° C. The conditions and results are summarized in Table I below.

TABLE I

| Temp. °C | WHSV | Tol. Conv. Mole % | Selectivity, % | | % Para in Xylene Product |
|---|---|---|---|---|---|
| | | | Benzene | Xylenes | |
| 450 | 3.6 | 7.4 | 43.5 | 55.5 | 24.7 |
| 500 | 3.5 | 20.5 | 44.6 | 53.8 | 24.5 |
| 550 | 3.5 | 38.8 | 48.0 | 48.8 | 24.2 |
| 600 | 3.5 | 49.2 | 54.4 | 41.7 | 24.1 |

It will be seen from the above results that the unmodified catalyst afforded a xylene product in which the para isomer was present in its normal equilibrium concentration of approximately 24 weight percent of the xylene fraction.

EXAMPLE 2

A catalyst of HZSM-5 modified by the addition thereto of 3.45 weight percent of phosphorus was prepared by suspending 33.5 grams of large crystal, anhydrous HZSM-5 in 167.5 ml of dry n-octane in a flask fitted with a condenser and dry nitrogen purge. After starting to heat the flask, 13.2 ml of trimethylphosphite were added and the contents slurried to obtain a uniform solution in the octane. The slurry was gently refluxed overnight (about 16 hours). After cooling, the slurry was filtered, the catalyst washed with 250 ml of $CH_2Cl_2$ followed by 250 cc of pentane. After 2 hours in a vacuum oven at 110° C., the catalyst was placed in an oven at 500° C., in air, for a period of 16 hours.

This catalyst was conditioned before use by calcination in a stream of air at 150 cc/minute, at 550° C. for a period of 2 hours. Following this, it was treated with a 50/50 volume $CH_3OH/H_2O$ solution at 550° C. for 16 hours at a WHSV of 16 hours.

This catalyst was used for disproportionating toluene by passage thereof over 6.0 grams of the catalyst at a weight hourly space velocity of 3.5 at a temperature between 550° C. and 650 ° C. The conditions and results are summarized in Table II below.

TABLE II

| Temp, °C | WHSV | Tol. Conv. Mole % | Selectivity, % Benzene | Selectivity, % Xylenes | % Para in Xylene Product |
|---|---|---|---|---|---|
| 550 | 3.5 | 0.4 | 42.9 | 57.1 | 41.2 |
| 600 | 3.5 | 1.2 | 46.2 | 53.8 | 39.4 |
| 650 | 3.5 | 2.3 | 50.1 | 48.6 | 37.7 |

It will be seen from the above results that under comparable reaction conditions, the amount of para-xylene in the xylene fraction increased approximately 65 percent as a result of the presence of phosphorus in the catalyst.

EXAMPLE 3

A catalyst of HZSM-5 modified by the addition thereto of 3.45 weight percent of phosphorus was prepared as in Example 2. However, in contrast with Example 2, this catalyst was not treated further before use.

This catalyst was used for disproportionating toluene by passage thereof over 6.0 grams of the catalyst at a weight hourly space velocity of 3.5 at a temperature between 550° C. and 700° C. The conditions and results are summarized in Table III below.

TABLE III

| Temp. °C | WHSV | Tol. Conv. Mole % | Selectivity, % Benzene | Selectivity, % Xylenes | % Para in Xylene Product |
|---|---|---|---|---|---|
| 550 | 3.5 | 0.3 | 48.4 | 51.6 | 57.2 |
| 600 | 3.5 | 0.7 | 47.6 | 52.4 | 50.4 |
| 650 | 3.5 | 1.7 | 50.4 | 47.8 | 48.5 |
| 700 | 3.5 | 3.1 | 59.5 | 36.7 | 61.9 |

Again, it will be evident that under comparable reaction conditions, the amount of para-xylene in the xylene fraction was very substantially increased, i.e. more than doubled, by use of the phosphorus-modified catalyst.

EXAMPLE 4

Ten grams of large crystal HZSM-5 were suspended in a solution of 4.16 grams of 85% $H_3PO_4$ in 150 ml. of methanol. After gently refluxing for about 16 hours, the solvent was boiled off. The remaining solid was placed in an oven at 150° C. about 3 hours and then placed in a furnace at 500° C. in air, in an open dish for 4.5 hours. Analysis of this catalyst indicated the presence of 8.51 weight percent phosphorus.

Two grams of this catalyst were treated with toluene in the vapor phase at atmospheric pressure. The conditions of reaction and products obtained are summarized in Table IV below.

TABLE IV

| Temp. °C | WHSV | Tol. Conv. Mole % | Xylenes para | Xylenes meta | Xylenes ortho | Product Selectivity, Wt % Benzene | Product Selectivity, Wt % Xylenes |
|---|---|---|---|---|---|---|---|
| 550 | 10.6 | 0.4 | 100 | 0 | 0 | 45.9 | 54.1 |
| 600 | 10.5 | 0.8 | 100 | 0 | 0 | 48.8 | 51.2 |
| 550 | 4.0 | 0.8 | 95.1 | 4.9 | 0 | 45.3 | 54.7 |
| 600 | 4.0 | 1.4 | 94.6 | 5.4 | 0 | 49.2 | 50.8 |

From the above results it will be seen that high selectivities to the para-isomer were obtained in the xylene product, and that only benzene and xylenes were detected in the product.

EXAMPLE 5

Ten grams of large-crystal HZSM-5 were placed in a vacuum dessicator, over a dish of water, evacuated at room temperature with an aspirator and allowed to stand overnight. An increase in weight of 1.75 grams was observed due to adsorption of water. To this was added 8.0 grams of diphenylphosphine chloride in 150 ml. of toluene. The suspension was brought to reflux and held for 17 hours. At this point, the solvent was boiled off and the remaining catalyst placed in a dish and then put in an oven at 150° C. for 2½ hours and thereafter placed in a furnace, in air, at 500° C. for 5 hours. Analysis of this catalysis indicated the presence of 5.08 weight percent phosphorus.

Two grams of this catalyst were treated with toluene in the vapor phase at atmospheric pressure. The conditions of reaction and product obtained are summarized in Table V below.

TABLE V

| Temp, °C | WHSV | Tol. Conv. Mole % | Xylenes para | Xylenes meta | Xylenes ortho | Product Selectivity, Wt % Benzene | Product Selectivity, Wt % Xylenes |
|---|---|---|---|---|---|---|---|
| 550 | 10.6 | 0.9 | 92.6 | 7.4 | 0 | 43.7 | 56.3 |
| 600 | 10.6 | 1.4 | 92.0 | 8.0 | 0 | 45.3 | 54.7 |
| 550 | 4.3 | 2.2 | 80.8 | 13.9 | 5.3 | 43.4 | 56.6 |
| 600 | 4.3 | 3.7 | 79.5 | 14.9 | 5.7 | 45.3 | 54.7 |

From the above results, it is again evident that high selectivities to the para-isomer were obtained in the xylene product and that only benzene and xylene products were detected.

It is to be understood that the foregoing description is merely illustrative of preferred embodiments of the invention of which many variations may be made by those skilled in the art within the scope of the following claims without departing from the spirit thereof.

I claim:

1. A process for effecting disproportionation of toluene to produce benzene and xylenes in which the proportion of para-xylene isomer is in excess of its normal equilibrium concentration which comprises contacting toluene under conditions effective for accomplishing said disproportionation in the presence of a catalyst comprising a crystalline aluminosilicate zeolite, said zeolite having a silica to alumina ratio of at least about 12, a constraint index within the approximate range of 1 to 12, said catalyst having been modified by the addition thereto of phosphorus in an amount of at least about 0.5 percent by weight.

2. The process oc claim 1 wherein said crystalline aluminosilicate zeolite is characterized by a silica/allumina ratio in excess of 30.

3. The process of claim 1 wherein said crystalline aluminosilicate zeolite is ZSM-5.

4. The process of claim 1 wherein phosphorus addition is accomplished as a result of contact of the crystalline aluminosilicate zeolite with a phosphorus compound.

5. The process of claim 1 wherein phosphorus is present in an amount of between about 0.5 and about 25 weight percent.

6. The process of claim 1 wherein of claim 1 wherein said phosphorus is present in an amount of between about 2 andd about 15 weight percent.

7. The process of claim 1 wherein the disproportionation conditions include a temperature of between about 800°F. and about 1400°F., a pressure between atmospheric and about 1000 psig and a weight hourly space velocity between about 0.5 and about 20.

8. The process of claim 1 wherein the crystalline aluminoxilicate zeolite is combined in an amount between about 1 and about 90 weight percent in a binder therefor.

9. The process of claim 8 wherein said binder is alumina.

10. The process of claim 1 wherein the crystalline aluminosilicate zeolite is predominately in the hydrogen form.

11. The process of claim 3 wherein the ZSM-5 zeolite is predominately in the hydrogen form.

12. The process of claim 7 wherein the crystalline aluminosilicate zeolite is ZSM-5.

13. The process of claim 12 wherein the ZSM-5 zeolite is predominately in the hydrogen form.

* * * * *

UNITED STATES PATENT AND TRADEMARK OFFICE
CERTIFICATE OF CORRECTION

PATENT NO. : 4,016,219
DATED : April 5, 1977
INVENTOR(S) : WARREN W. KAEDING

It is certified that error appears in the above-identified patent and that said Letters Patent are hereby corrected as shown below:

Column 3, line 10, "50%" should be --60%--.
Column 4, line 65, In line 65, delete "providing said zeolite to have increased capacity".
Column 11, line 50 after "28.9 weight percent" --$SiO_2$, 8.9 weight percent-- should be added.
Column 16, line 6, "The process of Claim 1 wherein of Claim 1 wherein" should be --The process of Claim 1 wherein--.
Column 16, line 15, "aluminoxilicate" should be --aluminosilicate--.

Signed and Sealed this

Twentieth Day of September 1977

[SEAL]

Attest:

RUTH C. MASON
*Attesting Officer*

LUTRELLE F. PARKER
*Acting Commissioner of Patents and Trademarks*